(12) United States Patent
Kreidler et al.

(10) Patent No.: US 9,393,332 B2
(45) Date of Patent: Jul. 19, 2016

(54) FILTER HOLDER FOR STERILIZATION CONTAINER

(71) Applicant: Innovation Medical GmbH, Tuttlingen (DE)

(72) Inventors: Winfried Kreidler, Tuttlingen (DE); Jochen Kreidler, Tuttlingen (DE)

(73) Assignee: Innovation Medical GmbH, Tuttlingen (DE)

( * ) Notice: Subject to any disclaimer, the term of this patent is extended or adjusted under 35 U.S.C. 154(b) by 175 days.

(21) Appl. No.: 14/170,922

(22) Filed: Feb. 3, 2014

(65) Prior Publication Data

US 2015/0053703 A1   Feb. 26, 2015

(30) Foreign Application Priority Data

Aug. 23, 2013   (DE) .................... 20 2013 007 581 U (51) Int. Cl.
*A61L 2/26*   (2006.01)
(52) U.S. Cl.
CPC ............. *A61L 2/26* (2013.01); *A61L 2202/182* (2013.01)
(58) Field of Classification Search
CPC .... A61L 2/26; A61L 2202/182; A61B 50/30; A61B 2050/006; A61B 2050/0063
USPC ............................................ 220/293; 55/492
See application file for complete search history.

(56) References Cited

U.S. PATENT DOCUMENTS

| | | | |
|---|---|---|---|
| 3,788,658 A * | 1/1974 | Benjamin | B23B 31/06 279/155 |
| 4,783,321 A * | 11/1988 | Spence | A61L 2/26 206/439 |
| 5,277,876 A * | 1/1994 | Wagner | A61L 2/26 137/72 |
| 5,324,489 A * | 6/1994 | Nichols | A61L 2/26 206/363 |
| 2001/0020601 A1* | 9/2001 | Gabele | A61L 2/26 210/348 |
| 2002/0149200 A1* | 10/2002 | Fumioka | A61M 39/1011 285/81 |
| 2004/0256268 A1* | 12/2004 | Gleichauf | A61L 2/26 206/438 |
| 2004/0256269 A1* | 12/2004 | Gleichauf | A61L 2/022 206/439 |
| 2005/0045551 A1* | 3/2005 | Jakab | A61L 2/022 210/436 |
| 2007/0084862 A1* | 4/2007 | Jakab | A61L 2/022 220/4.01 |
| 2012/0006366 A1 | 1/2012 | Kreidler | |
| 2012/0189508 A1 | 7/2012 | Kreidler | |

FOREIGN PATENT DOCUMENTS

DE   20 2010 009 925 U1   10/2010
DE   20 2011 001 772 U1   4/2011

* cited by examiner

*Primary Examiner* — Fenn Mathew
*Assistant Examiner* — Robert Stodola
(74) *Attorney, Agent, or Firm* — McGlew and Tuttle, P.C.

(57) ABSTRACT

A filter holder, for a sterilization container (1), has a wall area (5) with ventilation openings (7), through which an exchange of air takes place between the interior space of the sterilization container and the surrounding area, covered by a filter sheet (10) to form a sterile barrier, sterilizing air entering the interior space. The filter sheet is held on the wall area (5, 6) by an air-permeable pressing disk. A holding pin (20), with a mounting hole (34), by which the pressing disk (12) can be pressed against the wall area in the axial direction (41), can be attached to a mounting pin (11), which is stationary relative to the wall area. The holding pin (20) is connected with the mounting pin in a pressed position via a detachable positive-locking connection (19, 51). The connection can be secured by an adjusting sleeve (21) mounted displaceably on the holding pin.

16 Claims, 8 Drawing Sheets

FILTER HOLDER FOR STERILIZATION CONTAINER

CROSS REFERENCE TO RELATED APPLICATIONS

This application claims the benefit of priority under 35 U.S.C. §119 of German Utility Model Application DE 20 2013 007 581.3 filed Aug. 23, 2013, the entire contents of which are incorporated herein by reference.

FIELD OF THE INVENTION

The present invention relates to a filter holder for a sterilization container, which container is provided in a wall area or in a plurality of wall areas with ventilation openings, through which an exchange of air takes place in the closed state between the interior space of the sterilization container and the surrounding area, wherein the ventilation openings are covered by means of a filter sheet to form a sterile barrier, which brings about sterilization of the air entering the sterilization space through the ventilation openings, wherein the filter sheet is held on the wall area by an air-permeable pressing disk.

BACKGROUND OF THE INVENTION

Sterile containers, also called sterilization containers, comprise, as a rule, a box-shaped, lower container part and a container cover that can be placed tightly thereon. Such sterilization containers are known to be used to sterilize medical devices. The complete sterilization container is heated, as a rule, during the sterilization process, so that a diverse overpressure develops within the container. To make it possible to reduce this overpressure, such sterilization containers are provided in a wall area or in a plurality of wall areas with ventilation openings, through which the exchange of air with the surrounding area takes place.

To bring about sterilization of the entering ambient air especially during the cooling phase, during which ambient air enters the sterilization container for pressure equalization, such sterilization containers are usually equipped with a so-called sterile barrier. An air-permeable filter sheet, which fully covers the ventilation openings, is used as a sterile barrier in some embodiment variants. Various constructions, in which an air-permeable pressing disk is used to hold the filter sheet, are known in the state of the art for fixing such a filter sheet in the wall area of the ventilation openings tightly and sealingly.

Reference should be made in this connection, for example, to DE 20 2010 009 925 U1. A frame element, which has a ring-shaped design and is arranged stationarily in the area surrounding the ventilation openings within the corresponding wall area, is used in this constructions. The pressing disk has various perforations in this construction, so that the pressing disk itself is likewise permeable to air. A flat spring, which is provided with bayonet connection elements, is provided in this construction to hold the pressing disk or for pressing against the filter sheet placed on the inner wall in the area of the ventilation openings. The flat spring can be meshed and unmeshed with correspondingly associated bayonet connection elements of the frame element by means of these bayonet connection elements. Furthermore, the flat spring can be rotated about a common central axis of rotation in relation to the pressing disk, and the pressing disk is held in the frame element nonrotatably during the rotary adjustment of the flat spring.

Thus, a plurality of components are used in this construction to press the filter sheet stationarily against the inner wall of the wall area with the ventilation openings.

Furthermore, another construction, in which the pressing disk presses the filter sheet on the top side by means of special locking connections via a ball catch connection, is known from DE 20 2011 001 772 U1. The pressing disk is designed as a round disk in this construction and has a circular locking groove on the outside, with which the pressing disk can be brought lockingly in connection with locking elements.

These locking elements are arranged for this in the circumferential area of the ventilation openings and thus of the mounted pressing disk in a uniformly distributed pattern. Each locking element is designed as a separate component and arranged stationarily in mounting holes of ring segments projecting axially over the wall area extending at right angles to the wall area.

The locking elements are formed from an approximately cylindrical housing block, which is provided with a radial hole extending at right angles. A locking ball, which meshes (engages) radially inwardly with the locking groove of the pressing disk in the mounted state, is received in the radial hole adjustably in a spring-loaded manner. The housing block of the locking element is fixed stationarily in the respective mounting hole, for example, by means of a spring-type straight pin.

It is advantageous according to the devices of DE 20 2010 009 925 U1 and DE 20 2011 001 772 U1 that the pressing disk can be pressed onto the filter sheet without the pressing disk having to be rotated for fixation relative to the filter sheet, as this is known from the state of the art for previous constructions.

However, as it was already mentioned above, these constructions for holding the pressing disk have very complicated designs. The handling of the bayonet connections is also relatively unfavorable in DE 20 2010 009 925 U1, because the flat spring must first be aligned concentrically with the frame element and in the circumferential direction with its bayonet connection elements with the bayonet connection elements of the frame element for establishing these connections manually in order to be subsequently able to be rotated relative to the frame element.

It is additionally necessary in the subject of DE 20 2011 001 772 U1 to provide the pressing disk with a radially extending grip part, which must be located at a spaced location from the wall area of the sterilization container in order to make it possible to reach behind it. It shall be achieved by means of this grip part that the fingers can reach behind the pressing disk, so that the locking connections between the pressing disk and the locking balls can be released in a simple manner. The locking connections can be released by themselves in unfavorable cases in case of an impact on the container cover.

SUMMARY OF THE INVENTION

The basic object of the present invention is accordingly to design, based on the above-mentioned state of the art, a filter holder for a filter sheet (filter element) such that said filter holder can be handled in an extremely simple manner and it cannot, with certainty, be released by itself.

The object is accomplished according to the present invention with a filter holder for a sterilization container, which container is provided in a wall area or in a plurality of wall areas with ventilation openings, through which an exchange of air takes place in the closed state between the interior space of the sterilization container and the surrounding area, wherein the ventilation openings are covered by means of a filter sheet to form a sterile barrier, which brings about sterilization of the air entering the sterilization space through the ventilation openings, wherein the filter sheet is held on the wall area by an air-permeable pressing disk. A mounting pin, which projects over the wall area and is stationarily in connection with the wall area, is provided in the wall area of the ventilation openings. A holding pin is provided with a mounting hole, by which the pressing disk can be pressed against the wall area in the axial direction. The holding pin is able to be attached to the mounting pin, by the holding pin being in connection in its pressed state with the mounting pin via a detachable positive-locking connection. The positive-locking connection is able to be secured by means of an adjusting sleeve mounted displaceably on the holding pin.

Provisions may be made, according to further features of the invention, for the positive-locking connection between the mounting pin and the holding pin to comprise a circular locking groove of the mounting pin and a plurality of holding balls arranged in a radial through hole of the holding pin. The holding balls in the through holes are designed such that they can be radially adjusted from a neutral position, in which they are not in connection with the locking groove of the mounting pin, into a blocked position in which they mesh with the locking groove.

Further, provisions may be made according to further features of the invention for the adjusting sleeve to have a through hole for being pushed on the holding pin. The through hole has, in through hole end areas pointing towards the mounting pin, a circular, radial expansion, which is located in an upper, neutral axial position of the adjusting sleeve on the holding pin in the area of the holding balls and whose diameter is selected to be such that the holding balls can be moved radially into their neutral position, for the through hole with its holding balls, which has a smaller diameter, to be able to be brought into functional connection during an axial adjustment of the adjusting sleeve on the holding pin into its securing position such that the holding balls can be brought through the through hole into their blocked position, in which they protrude into the mounting hole of the holding pin and mesh with the locking groove of the mounting pin.

To adjust the adjusting sleeve on the holding pin in a defined manner, provisions may be made according to further features of the invention for the holding pin to have in its outer jacket surface an L-shaped groove, which forms a vertical section extending in parallel to the central longitudinal axis of the holding pin and a horizontal section extending at right angles thereto, for providing in the side wall of the adjusting sleeve a through hole, into which a fixing pin can be stationarily inserted, and for the fixing pin to pass through the side wall radially to the inside in the mounted state and to mesh with the L-shaped groove, for the adjusting pin to be able to be brought from its neutral upper axial position into its lower securing position axially along the vertical section and to be subsequently able to be caused to mesh with the horizontal section by a relative rotation in relation to the holding pin with its fixing pin into an axially nondisplaceable locking position. The adjusting sleeve and the holding pin are, furthermore, captively in connection with one another due to this design, so that when the adjusting sleeve is "raised," the holding pin is also "raised" at the same time via the fixing pin, which is in connection with the L-shaped groove thereof. Operation is considerably simplified hereby.

Further, provisions may be made according to further features of the invention for the holding pin to have in its upper end area a continuous through hole extending at right angles, in the radially outer end areas of which locking balls are provided, which are pressed radially outwardly by means of an axial compression spring, and for the through hole of the adjusting sleeve to have a circular fixing groove in its axially upper end area, and for the axial arrangement of the through hole in the holding pin and the axial arrangement of the fixing groove in the through hole of the adjusting sleeve to be selected to be such that the locking balls lockingly mesh with the fixing groove in the upper, neutral axial position of the adjusting sleeve. The upper, neutral axial position of the adjusting sleeve relative to the holding pin is secured due to this embodiment, so that an unintended adjustment of the adjusting sleeve in the axial direction is prevented from occurring.

The locked position of the adjusting sleeve on the holding pin is secured by the embodiment according to further features of the invention. Provisions are accordingly made for the through hole of the adjusting sleeve to have two mutually diametrically opposed milled recesses axially above their fixing groove and for the circumferential positions and the axial position of the milled recesses of the adjusting sleeve relative to the locking balls of the holding pin are selected to be such that the locking balls lockingly mesh with the milled recesses after the axial adjustment and rotation of the adjusting sleeve into the locked position thereof.

It is achieved through the embodiment according to further features of the invention that when the adjusting sleeve is raised together with the holding pin, the pressing disk is also raised at the same time. Furthermore, when the holding pin is placed on the mounting pin, the pressing disk is inevitably placed in its correct position on the filter sheet or in the area of the ventilation openings, so that the pressing disk does not need to be separately aligned in advance. Provisions are thus made for the pressing disk to be stationarily in connection with the holding pin.

It is achieved due to the embodiment according to further features of the invention that the holding pin may co-rotate during a relative rotation of the adjusting sleeve relative to the holding pin to release or establish the positive-locking connection, which contributes to reliable operability of the device according to the present invention. Accordingly, provisions are made for the mounting pin to have in its end area located towards the wall section a radially expanded profile web with holding surfaces arranged uniformly distributed on the circumference and for the mounting hole of the holding pin to have in its end area located towards the wall section a bearing profile, with which the holding pin meshes nonrotatably in its pressed position with the holding surfaces of the profile web.

Due to the embodiment of the filter holder according to the present invention, comprising the pressing disk, the mounting pin, the holding pin with its adjusting sleeve and the corresponding positive-locking connection, extremely simple handling is achieved during the replacement of a filter sheet. Thus, the complete filter holder can be detached by a simple rotary and axial motion and fixed again correspondingly in the opposite direction.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
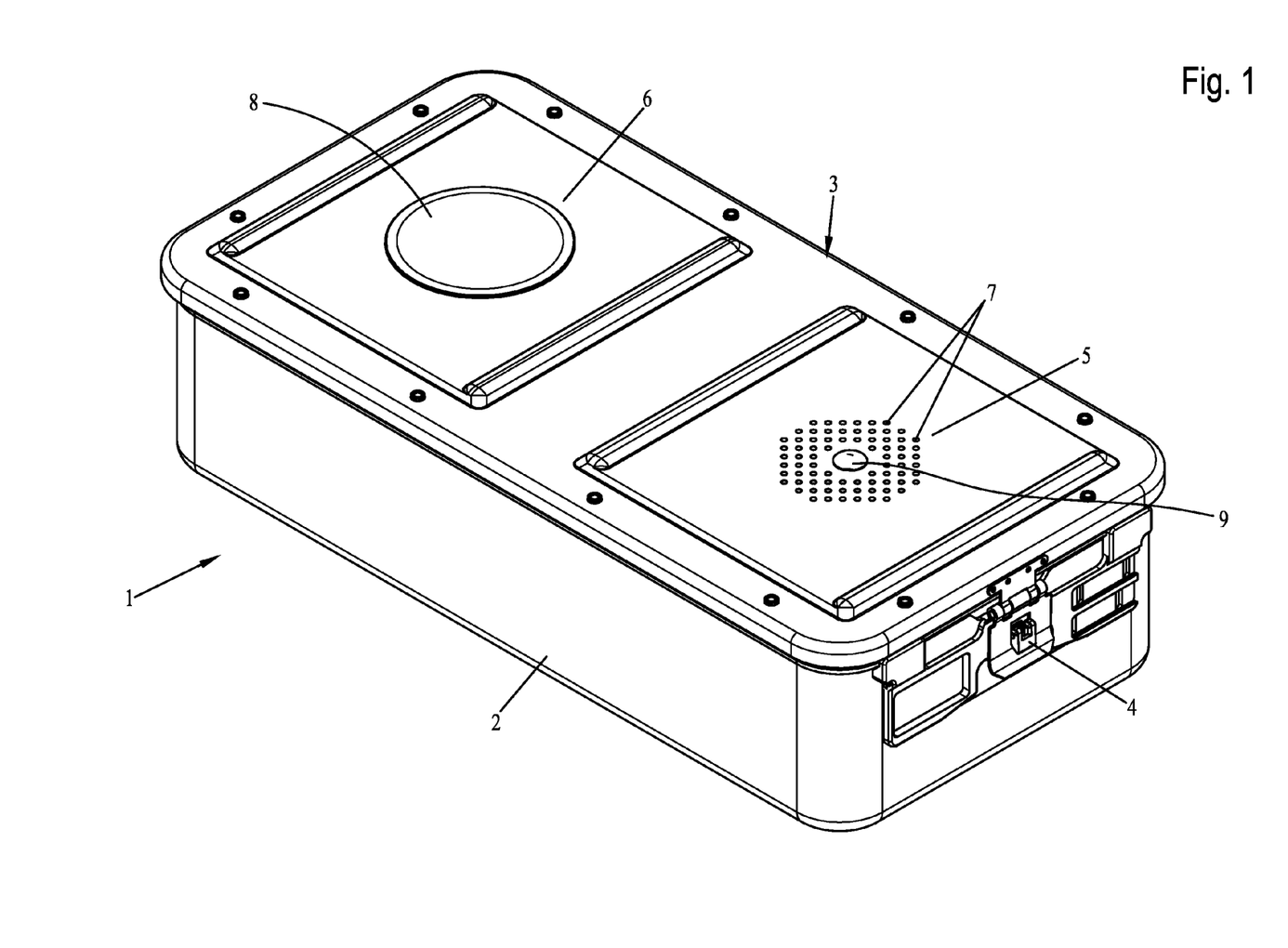
FIG. 1 is an embodiment variant of a sterilization container, comprising a lower container part as well as a container cover.

Referring to the drawings in particular, FIG. 1 shows as an example a sterilization container 1, which has a box-shaped design in this exemplary embodiment and has a lower container part 2. A container cover 3 is placed tightly on this lower container part 2, and said container cover is held in this attached position by means of two container closures 4, but only the "front" container closure 4 is visible in FIG. 1.

Further, it can be seen in FIG. 1 that the container cover 3 has two wall areas 5 and 6 in the present exemplary embodiment, which are provided with a plurality of ventilation openings 7 each. The ventilation openings 7 of the wall area 6 are shown in the bottom view in FIG. 2.

The two wall areas 5 and 6 with their ventilation openings 7 differ in that the ventilation openings in the second wall area 6 are covered by a cover plate 8. This cover plate 8 is located at a vertically spaced location from the wall area 6, so that ambient air can flow through the ventilation openings 7 visible from FIG. 2.

Furthermore, it is seen in FIG. 1 that a flat lock nut 9, whose significance will be explained in more detail below, is provided centrally within the ventilation openings 7 of the wall area 5.

The ventilation openings 7 are used for "pressure equalization" within the closed sterilization container 1 during operation. Thus, such a sterilization container 1 is used, as was mentioned already in the introduction to the specification, for example, to sterilize surgical instruments. The surgical instruments are placed for this purpose into the sterilization container 1, the container cover 3 is placed on the container part 2 and closed tightly. The sterilization container 1 is heated, as a rule, during the sterilization process, so that an overpressure develops within this sterilization container 1. The air now flows through the ventilation openings 7 from the inside to the outside for pressure equalization.

The sterilization container 1 is cooled again after the sterilization operation, so that ambient air flows through the ventilation openings 7 into the sterilization container 1 in the opposite direction. To prevent contamination within the container or of the sterilized medical instruments for hygienic reasons, a so-called sterile barrier is provided, which is in the form of a filter sheet 10 in the embodiment variant shown and is shown as a separate component in FIG. 2.

Figure 2:
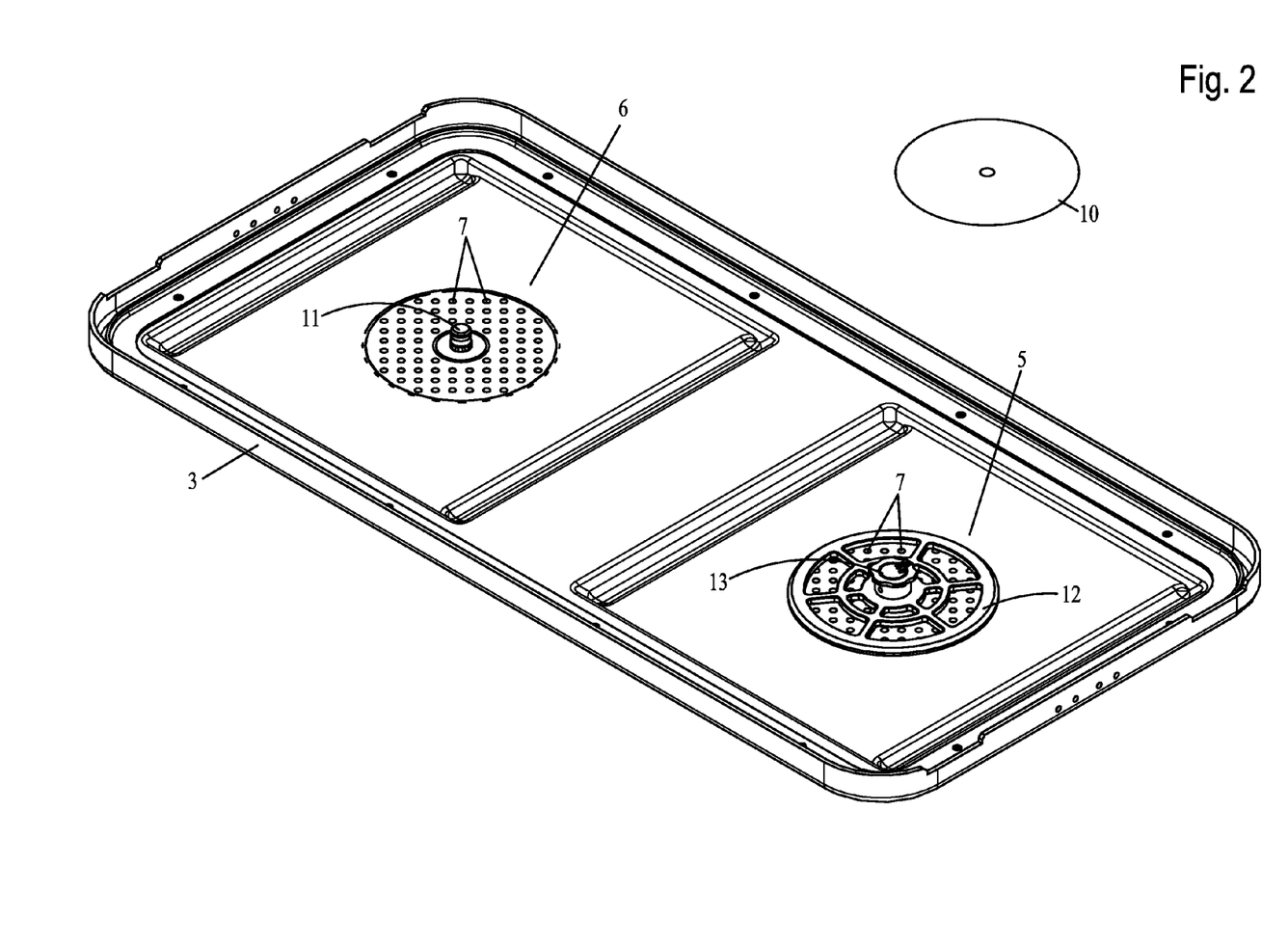
FIG. 2 is a perspective bottom view of the container cover of the sterilization container from FIG. 1.

As can be seen further from the bottom view of the container cover 3 in FIG. 2, a mounting pin 11, which is screwed into a corresponding threaded hole of the wall area 6 of the container cover 3, which said threaded hole is not visible in FIG. 2, is provided centrally in the wall area 6 or in the area of the ventilation openings 7. The cover plate 8, which is screwed onto a threaded section, which protrudes on the top side above the wall section 6 of the container cover 3, is used in the area of the container cover 3 to secure this mounting pin 11.

After the mounting pin 11 has been positioned, the filter sheet 10 can be placed on same in the area of the ventilation openings 7. As is shown for the wall area 5 in FIG. 2, a pressing disk 12, which is braced on the top side against the filter sheet 10 via a special holding device 13 in the exemplary embodiment shown, is subsequently placed on the filter sheet 10. The holding device 13 thus forms a filter holder together with the pressing disk 12 for stationarily holding the filter sheet 10 in the area of the ventilation openings 7.

Figure 3:
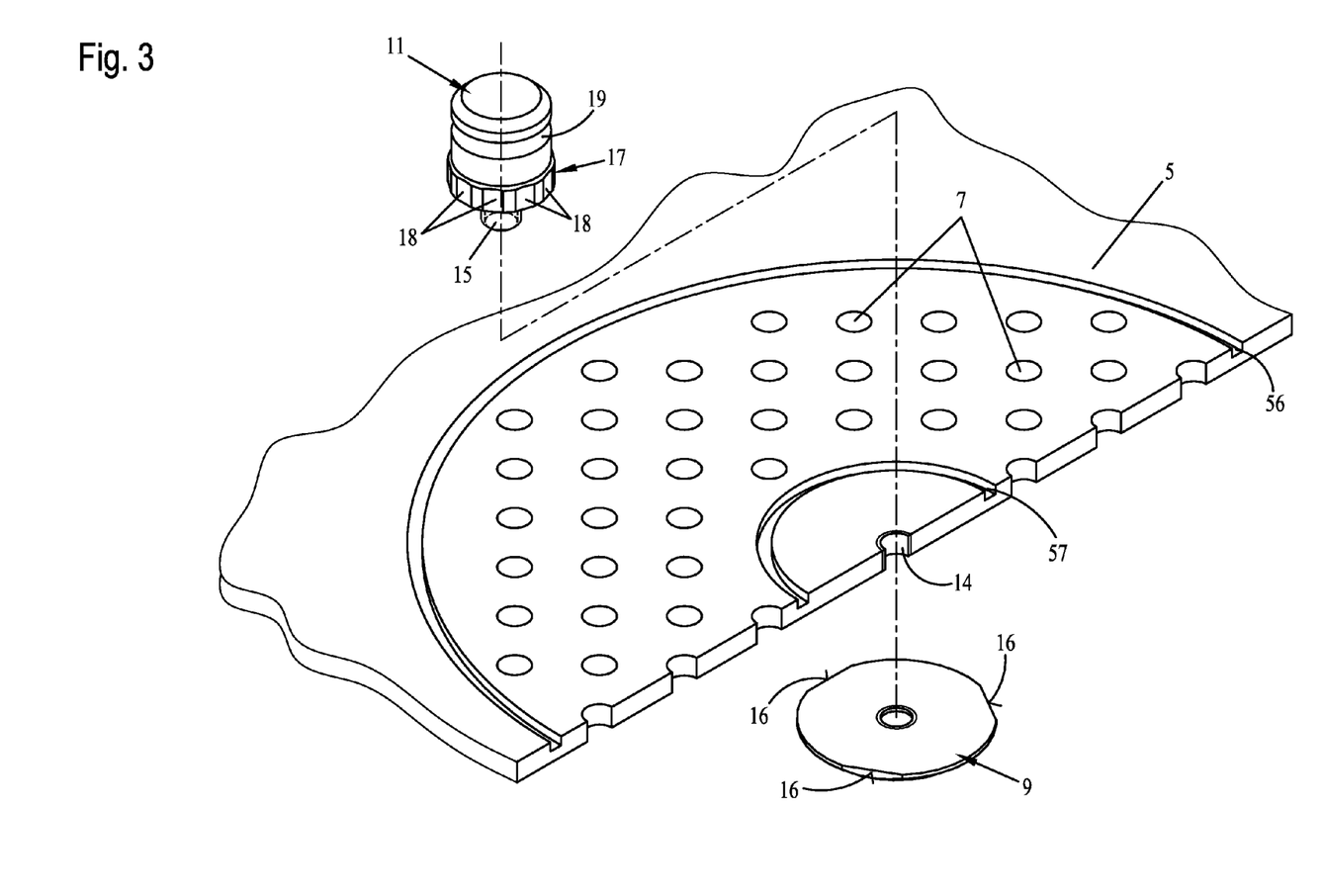
FIG. 3 is a perspective partial view of a wall area of the container cover from FIG. 2 in a bottom view in the area of ventilation openings with a mounting pin as well as with a lock nut, which can be arranged stationarily centrally in the area of the ventilation openings.

FIG. 3 shows for this a partial sectional view of the wall area 5 with the ventilation openings 7. It can be recognized that an internal screw thread, into which a threaded pin 15 of the mounting pin 11 can be screwed, is provided centrally in the area of the ventilation openings 7. The axial length of this threaded pin 15 is selected here to be such that this threaded pin passes through the wall area 5 in the mounted state. The lock nut 9 can be correspondingly screwed onto this threaded pin 15, so that the mounting pin 11 is arranged stationarily in the wall area 5. To make it possible to screw the lock nut 9 onto the threaded pin 15 in a tightly seated manner, said lock nut has, on the whole, three flat wrench contact surfaces 16 arranged uniformly distributed on the circumference in the exemplary embodiment being shown.

Further, it can be recognized from FIG. 3 that the mounting pin 11 has, in its end area located towards the threaded pin 15, a radially expanded profile web 17, which forms a plurality of flat holding surfaces 18 distributed uniformly on the circumference. In the opposite end area of this profile web 17, the mounting pin 11 has a circular locking groove 19, which has an approximately partly cylindrical cross-sectional shape.

As was already mentioned in connection with FIG. 2, the holding device 13 can be detachably placed on this mounting pin 11 in the mounted state.

Figure 4:
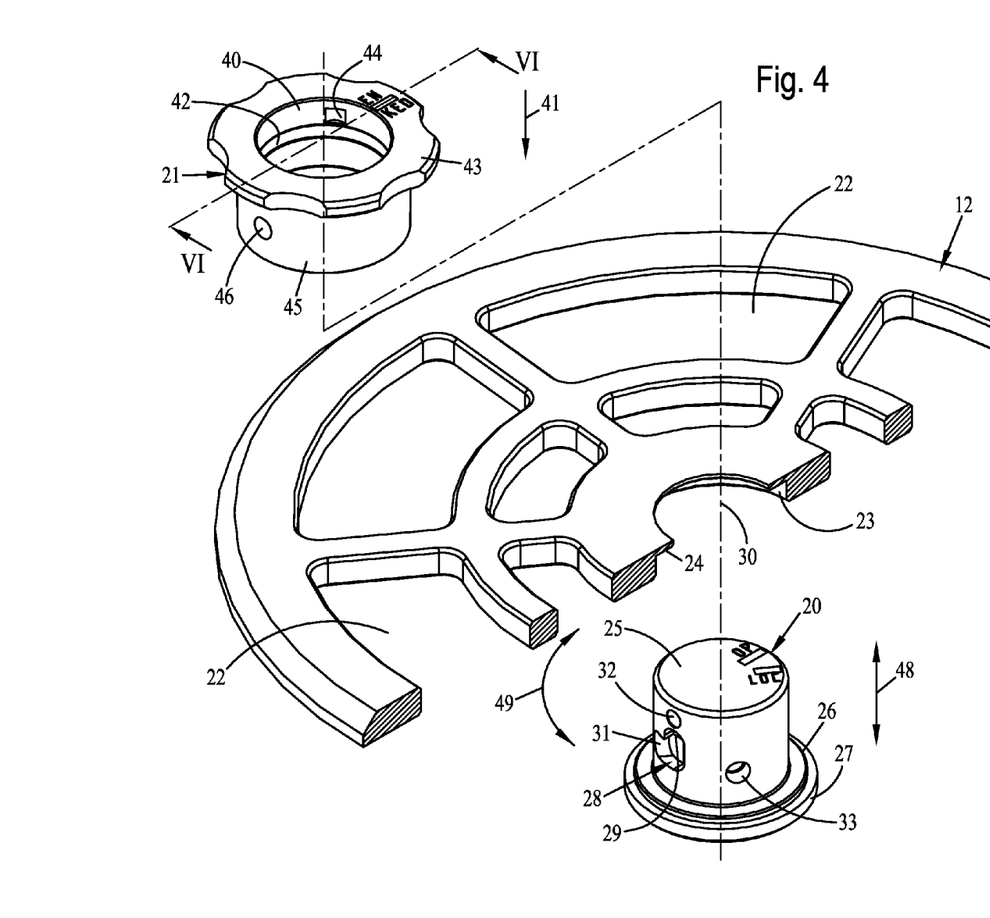
FIG. 4 is an exploded perspective view of a pressing disk shown in a partial section together with a holding pin as well as with an adjusting sleeve.

FIG. 4 shows for this a partial perspective view of the pressing disk 12 from FIG. 2 together with a holding pin 20 and with an adjusting sleeve 21. This holding pin 20 and the adjusting sleeve 21 together form the holding device 13 mentioned in connection with FIG. 2 for the pressing disk 12. The pressing disk 12 has a plurality of perforations 22, so that an air flow can flow correspondingly through these. The pressing disk 12 is provided centrally with an internal screw thread 23, which is limited on the top side by means of a radially inwardly protruding stop web 24.

Corresponding to the diameter of this stop web 24, the holding pin 20 has a vertically upwardly projecting cylindrical bearing section 25.

In the lower end area of this bearing section 25, the holding pin 20 forms a radially projecting, circular mounting web 26, which is provided with a corresponding external screw thread 27 (not shown explicitly in the drawing). For mounting in the pressing disk 12, the holding pin 20 can be passed with its cylindrical bearing section 25 through the stop web 24 and can be caused to stationarily mesh by its external screw thread 27 with the internal screw thread 23 of the pressing disk 12.

Further, it can be seen in FIG. 4 that the cylindrical bearing section 25 of the holding pin 20 has, in its jacket surface in the front left area, an L-shaped groove 28, which has a vertical section 29 towards the upper end area, which said vertical section extends in parallel to the central longitudinal axis 30 of the bearing section 25 or of the holding pin 20. The L-shaped groove 28 forms a horizontal section 31 extending at right angles in the lower end area of this vertical section 29.

Figure 5:
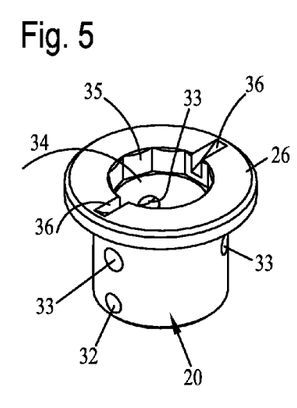
FIG. 5 is the holding pin from FIG. 4 in a perspective bottom view.

Further, it can be recognized from FIG. 4 and also from the bottom view of the mounting pin 20 in FIG. 5 that a through hole 32 is provided in the free end area of the bearing section 25. This through hole 32 is used to receive two locking balls, between which an axial compression spring is provided, as this will be explained in more detail below.

In the area located towards the mounting web 26, the bearing section 25 has a total of three mounting holes 33 (FIG. 5), which are used to receive a fixing element in the form of a locking ball, as this will be explained in more detail below.

Further, it can be recognized from FIG. 5 that the holding pin 20 has a central mounting hole 34, with which this holding pin 20 can be placed fittingly onto the mounting pin 11 from FIG. 3. Further, this mounting hole 34 in the axial end area of the mounting web 26 is provided with a bearing profile 35, with which the holding pin 20 can be placed fittingly onto the holding surfaces 18 of the profile web 17 of the mounting pin 11. The holding pin 20 can thus be arranged on the mounting pin 11 secured against rotation in the mounted state.

Further, it can also be seen in FIG. 5 that two grooves 36, which are used to firmly tighten the holding pin 20 in the internal screw thread 23 of the pressing disk 12, are arranged in the area of the mounting web 26 on the underside in the front surface of said mounting web.

Further, it can be seen in FIG. 4 that the adjusting sleeve 21 forms a central through hole 40, which has an inner fixing groove 42 at an axially spaced location from its upper front surface in the direction of arrow 41.

In the upper end area, the adjusting sleeve 21 has a radially expanded, profiled actuating web 43, which is used for the simplified operation of the adjusting sleeve 21. In the area between the inner fixing groove 42 and the upper front surface or in the area of this actuating web 43, the through hole 40 is provided with a milled recess 44, diametrically opposed to which a second milled recess 44, which is not recognizable in FIG. 4, may be arranged.

This milled recess or these milled recesses 44 is/are used during operation to fix a preset, relative angular position of the adjusting sleeve 21 relative to the holding pin 20. The milled recesses 44 will be overlapped with the through hole 32 in this position, so that the locking balls arranged in the through hole 32 under spring loading will come to mesh with these milled recesses 44.

Further, it can be recognized from FIG. 4 that the adjusting sleeve 21 has a through hole 46 in its cylindrical side wall 45.

Figure 6:
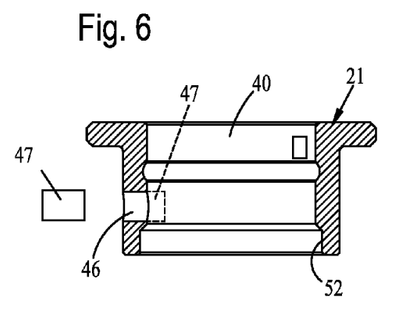
FIG. 6 is a sectional view VI-VI of the adjusting sleeve from FIG. 4.

As can be recognized from the sectional view of the adjusting sleeve 21 in FIG. 6, a fixing pin 47, which is seated stationarily in the through hole 46 in the mounted state and, as this is shown by broken lines in FIG. 6, protrudes into the through hole 46, can be caused to mesh with this through hole 46. This fixing pin 47 is inserted after attaching the adjusting sleeve 21 to the holding pin 20 and meshes in the mounted state with the L-shaped groove 28 or with the vertical section 29 or horizontal section 31 thereof as desired. It is thus achieved that the adjusting sleeve 31 is adjustable, on the one hand, limited to the holding pin 20 in the axial direction of the double arrow 48 and is likewise rotatable to a limited extent in the direction of the double arrow 49. The fixing pin 47 can be pressed, soldered or bonded into the through hole 46. A "clamping" threaded connection is also conceivable, so that the fixing pin 47 cannot become detached by itself in the through hole, which is designed as a threaded hole in this case.

Figure 7:
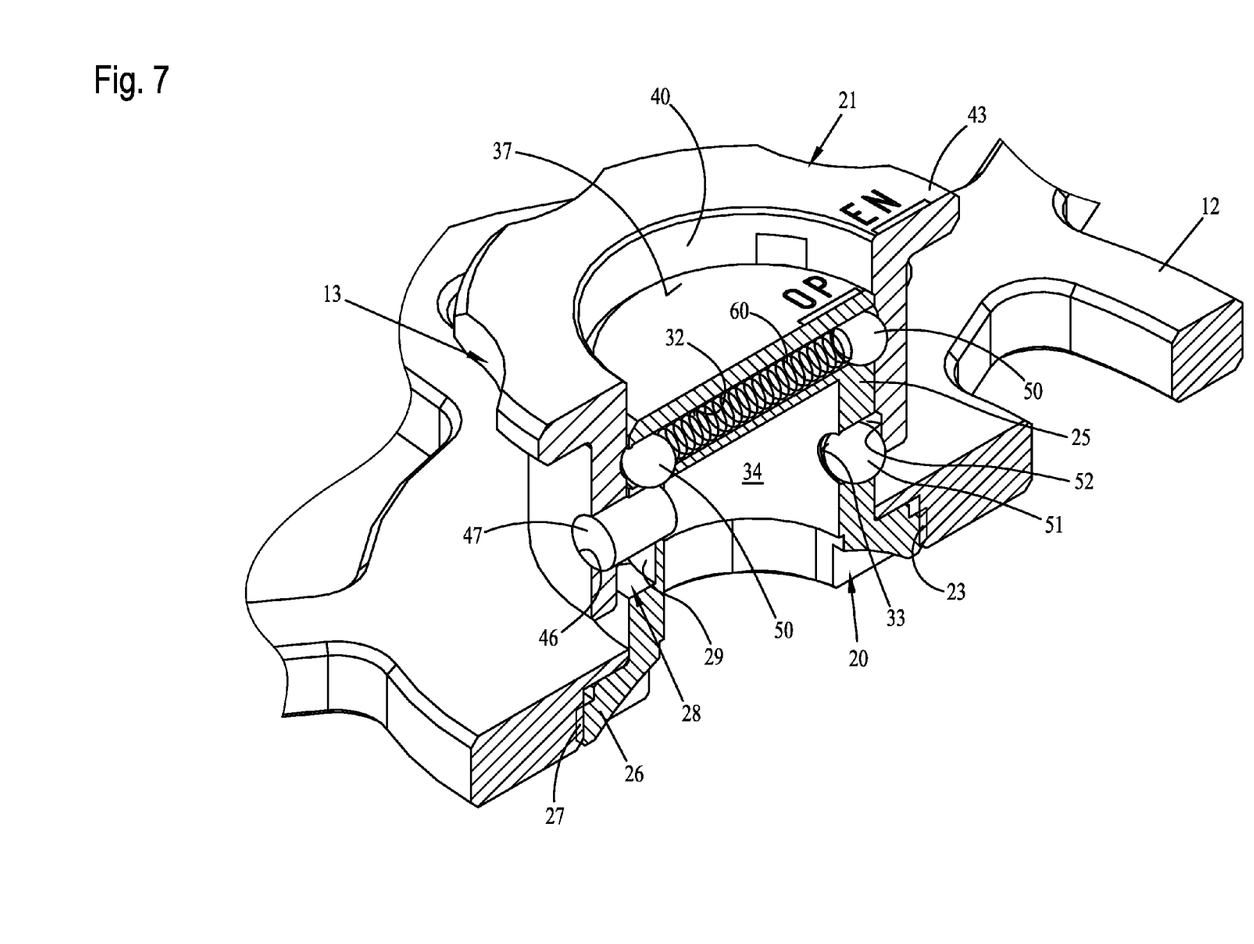
FIG. 7 is a perspective sectional view in the central area of the pressing disk with the holding pin mounted and with the adjusting sleeve from FIG. 4 attached.

Concerning the preassembled state of the pressing disk 12, of the holding pin 20 and of the adjusting sleeve 21, FIG. 7 shows an enlarged partial view of these components in the central area of the pressing disk 12.

It can be recognized from FIG. 7 that the adjusting sleeve 21 with its through hole 40 is attached to the cylindrical bearing section 25 of the holding pin 20. The adjusting sleeve 21 with its actuating web 43 is now located above the upper front surface 37 of the cylindrical bearing section 25. The above-mentioned two locking balls 50 shown in FIG. 7 mesh with the circular locking groove 42 of the adjusting sleeve 21 in this "neutral" position of the adjusting sleeve 21 relative to the holding pin 20. The neutral, axial relative position of the adjusting sleeve 21 relative to the holding pin 20 is thus secured.

Further, it can be recognized from FIG. 7 that the fixing pin 47 is arranged in the through hole 46 in a tightly seated manner and meshes with the vertical section 29 of the L-shaped groove 28 in the upper end area thereof. The adjusting sleeve 21 is thus fixed in this position against rotation against the holding pin 20 based on the functional connection of the fixing pin 47 with the vertical section 29 of the L-shaped groove 28.

Further, one of the three radial through holes 33 of the bearing section 25 from FIG. 5, in which a corresponding holding ball 51 is arranged, can also be recognized from FIG. 7. Further holding balls 51 are correspondingly inserted into the other two through holes not recognizable in FIG. 7 as well.

In this axial relative position of the adjusting sleeve 21 in relation to the holding pin 20, this holding ball 51 (or locking balls) is (are) located in an axial area of a radial expansion 52 of the through hole 40 of the adjusting sleeve 21, which is arranged in the lower end area of the adjusting sleeve 21, as this can also be recognized especially from the sectional view in FIG. 6. The holding ball 51 (or holding balls) can thus be moved radially to the outside until this comes into contact with this radial expansion 52 on the inside and does not protrude into the mounting hole 34 of the holding pin 20 any longer.

Furthermore, it can be recognized from FIG. 7 that the holding pin 20 with its external screw thread 27 of its mounting web 26 meshes with the internal screw thread 23 of the pressing disk 12 in a stationary manner.

The pressing disk 12 with the holding device 13 comprising the holding pin 20 and the adjusting sleeve 21 can be placed in this preassembled state onto the mounting pin 11 according to FIG. 3. Furthermore, FIG. 7 also shows the axial compression spring 60, by which the two locking balls 50 arranged in the end area of the through hole 32 extending at right angles are pressed radially outwardly under prestress.

Figure 8:
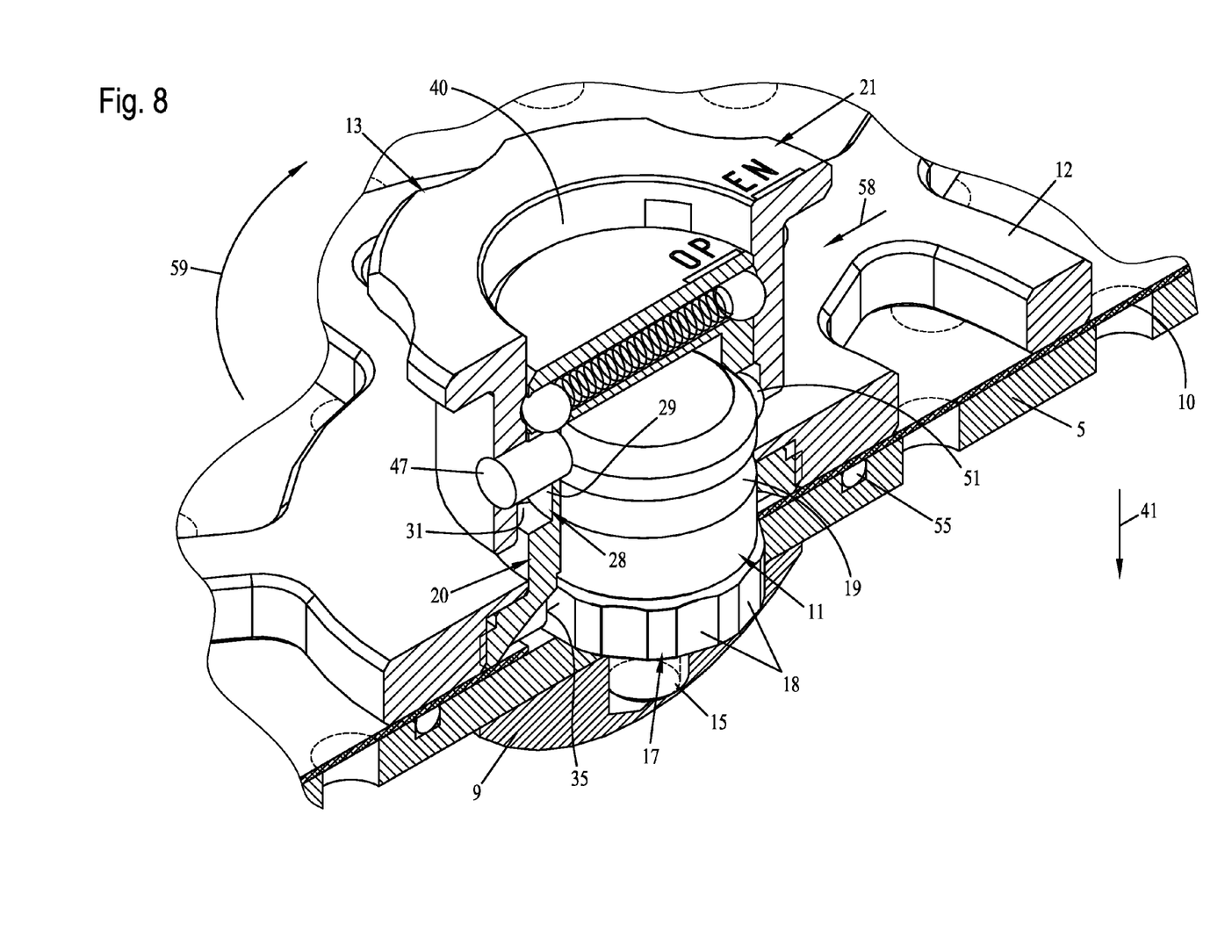
FIG. 8 is a perspective sectional view of the wall section with the ventilation openings of the container cover with the mounting pin mounted as well as with the pressing disk attached on this together with the holding pin that is stationarily in connection with the pressing disk and with the adjusting sleeve attached.

FIG. 8 shows the view from FIG. 7 with the pressing disk 12 of the holding device 13 in the state in which it is placed on the mounting pin 11. The mounting pin 11 is screwed into the wall section 5, and the lock nut 9 is screwed stationarily onto the threaded pin 15 of the mounting pin 11 on the underside. The mounting pin 11 is fixed nonrotatably on the wall area 5 in this mounted state of the mounting pin 11 in the wall area 5.

Further, it can be recognized that the holding ball 51 is located in the axial area of the circular locking groove 19 of the mounting pin 11 in this state in which the pressing disk 12 with the holding device 13 is placed "loosely" on the mounting pin 11. In this attached state, the holding pin 20 meshes with the holding surfaces 18 of the profile web 17 of the mounting pin 11 in a positive-locking manner and hence nonrotatably by its bearing profile 35, which can be recognized as a suggestion only in FIG. 8. Thus, the pressing disk 12 is also held nonrotatably in the wall area 5 based on the stationary threaded connection with the holding pin 20.

Further, it can be recognized from FIG. 8 that the filter sheet 10 shown as a separate component in FIG. 2 is arranged between the pressing disk 12 and the wall area 5. Furthermore, it can also be recognized from FIG. 8 that a sealing ring 55 is provided under the filter sheet 10.

Reference should briefly also be made in this connection to the view in FIG. 3, from which it can be recognized that a mounting groove 56, in which a second sealing ring, which is not shown explicitly in FIG. 3, is provided in the mounted state, is arranged in the outer circumferential area of the ventilation openings 7. To receive the sealing ring 55 from FIG. 8, the wall area 5 likewise has a circular mounting groove 57 in the area located radially within the ventilation openings 7.

To now press the pressing disk 12 at least slightly against the surface of the filter sheet 10 and especially to achieve a sealing action of the sealing ring 55, the adjusting sleeve 21 can be adjusted manually downwardly in the direction of arrow 41. The holding ball 51 (or holding balls) now enters (enter) the radially tapered through hole 40 from the area of the radial expansion 52 of the through hole 40, so that an adjusting motion of the holding ball 51 is brought about in the radial direction indicated by arrow 58. The holding ball 51 is thus pressed inevitably into the circular locking groove 19, as a result of which adjusting forces are, in turn, generated in the direction of arrow 41. Since a total of three such holding balls 51 are provided in the through holes 33 recognizable in FIG. 5, uniform pressing of the pressing disk 12 is brought about via these holding balls 51 and the locking groove 19 in the direction of arrow 41.

The fixing pin 47 "slides" along the vertical section 29 of the L-shaped groove 28 during this adjusting motion in the direction of arrow 41. When the "lower" end position of the adjusting sleeve 21 is reached, this fixing pin 47 is located in the axial area of the lower horizontal section 31 of the L-shaped groove 28. The fixing pin 47 can thus now be caused to mesh with the horizontal section 31 to fix this axial securing position of the adjusting sleeve 21 by rotating same in the direction of arrow 59 into its fixing position.

Figure 9:
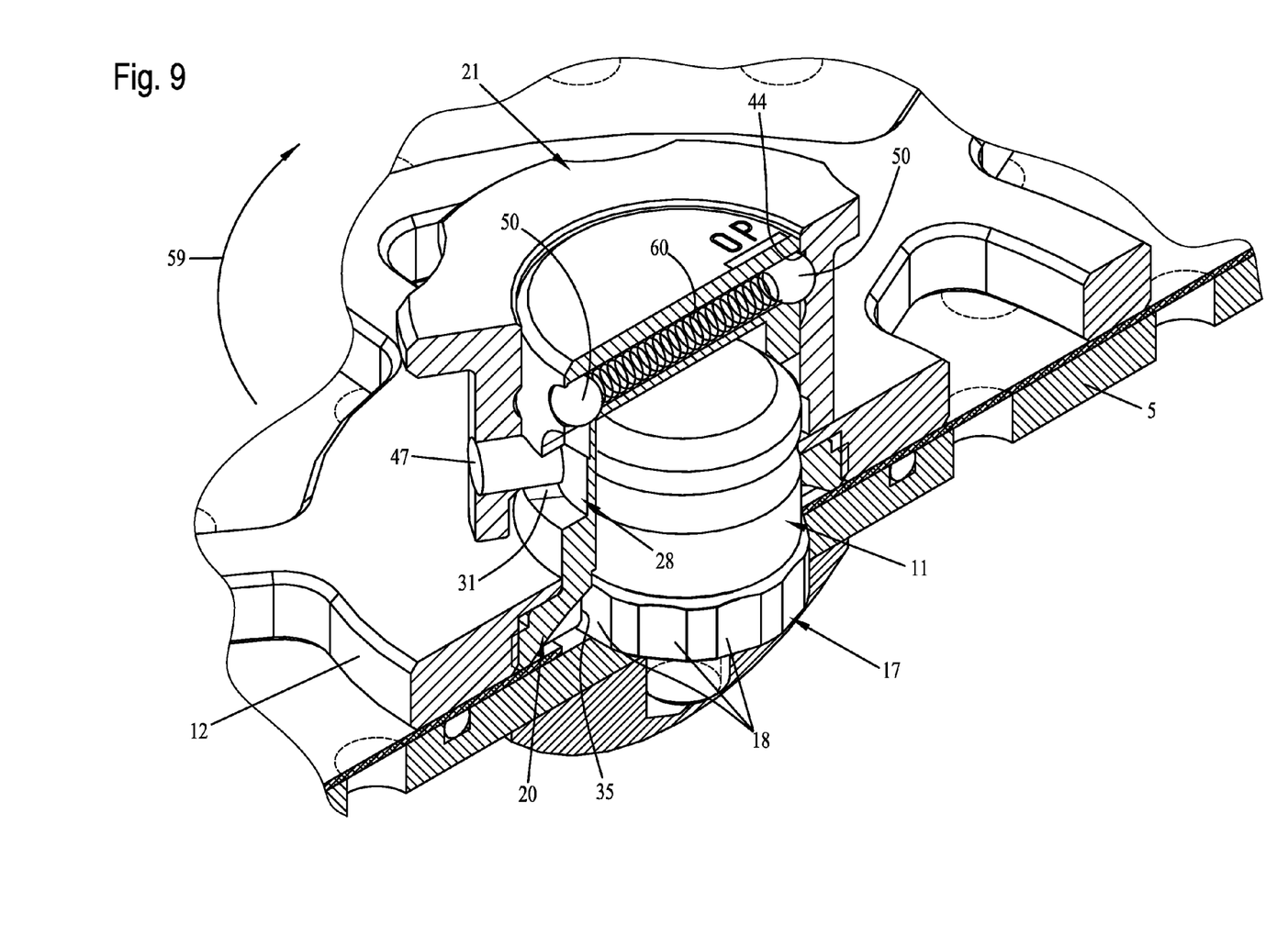
FIG. 9 is the view from FIG. 8 with the adjusting sleeve in its active securing position.

This fixed fixing position of the adjusting sleeve 21 with its fixing pin 47 can be recognized in the perspective sectional view shown in FIG. 9. It can also be recognized in this view that the locking ball 50 meshes with the milled recess 44 of the through hole 40 of the adjusting sleeve 21 and is held in this meshing position by the axial compression spring 60. The second locking ball 50 correspondingly meshes with the second milled recess not recognizable in FIG. 9. This meshing position of the second locking ball 50 with the second milled recess 44 is indicated by broken lines in FIG. 10, because this is not "actually" recognizable in FIG. 10 based on the section orientation from FIG. 9, because this is located "in front of" the plane of the drawing sheet.

As can also be determined from FIG. 9, the fixing pin 47 meshes with the horizontal section 31 of the L-shaped groove 28. Based on the positive-locking connection of the mounting pin 11 with the holding surfaces 18 of the profile web 17 with the inner bearing profile 35 of the holding pin 20, the holding pin 20 is likewise fixed nonrotatably relative to the wall section 5 on the mounting pin 11. It is thus ensured that the holding pin 20 cannot co-rotate during the rotary adjusting motion of the adjusting sleeve 21 in the direction of arrow 59.

Based on the meshing of the two locking balls 50 with the corresponding milled recesses 44 of the adjusting sleeve 21, the adjusting sleeve 21 is secured in this "locked" position.

Figure 10:
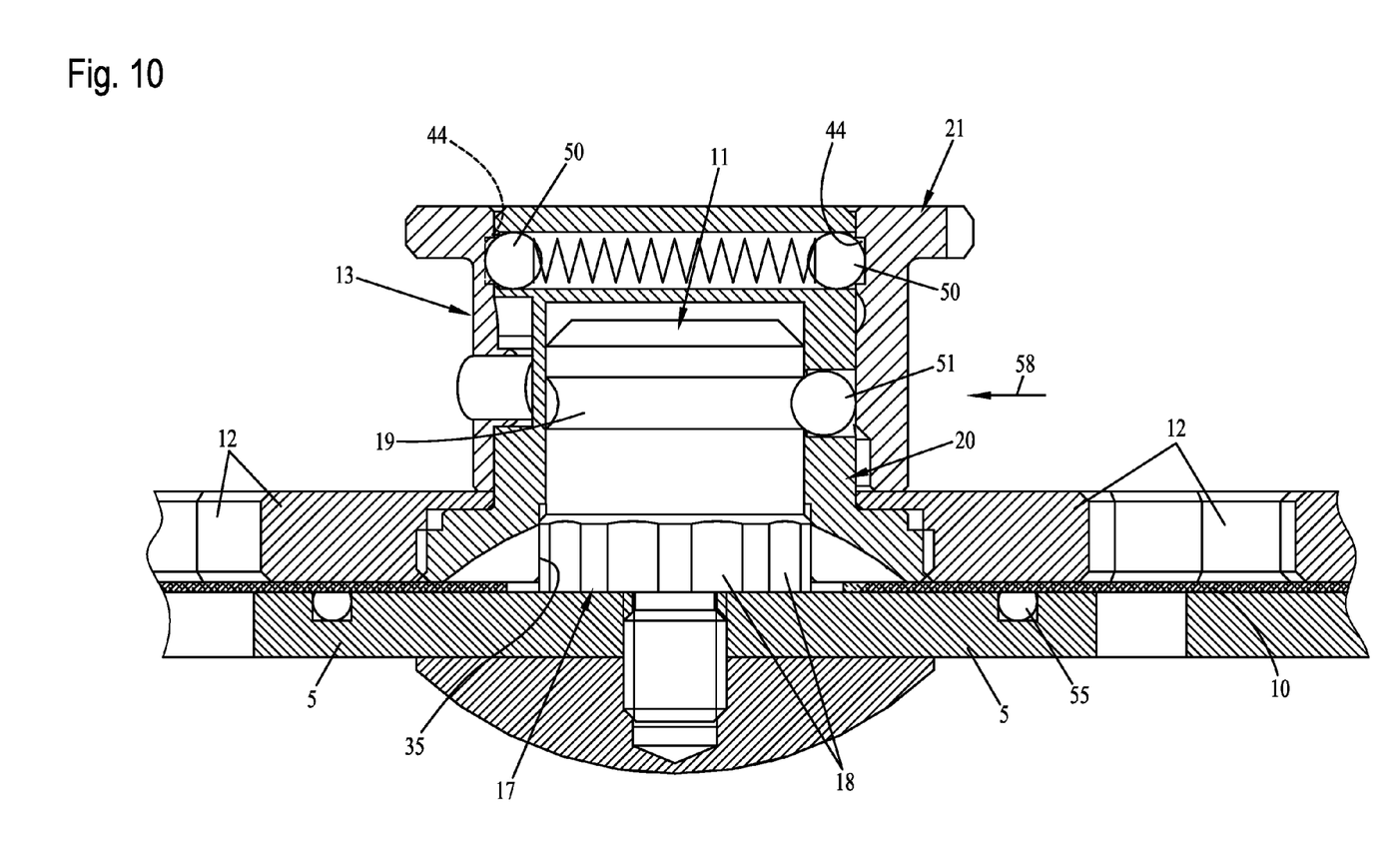
FIG. 10 is a sectional view of the wall section of the container cover from FIGS. 1 and 2 in the area of the ventilation openings thereof with the pressing disk locked.

Further, it can be determined from FIG. 10 that the holding ball 51, three of which are arranged distributed uniformly on the circumference, meshes with the locking groove 19 of the mounting pin 11. This locking ball 51 is supported at the inner wall of the through hole 40 of the adjusting sleeve 21, so that the locked position of the holding pin 20 is fixed securely together with the pressing disk 12. For example, the sealing ring 55 is compressed at least slightly in the wall area 5 in this fixed position, so that an optimal sealing action can be achieved here, as this can be recognized from FIG. 10.

By a correspondingly opposite rotary motion against arrow 59 from the locking position shown in FIGS. 10 and 9 and subsequently raising the adjusting sleeve 21 against arrow 41, the adjusting sleeve 21 with its radial expansion 52 will again reach the axial area of the locking balls 51, so that these are adjustable against arrow 58 radially outwardly until they come into contact with the inner wall of the radial expansion 52. The axial path of adjustment of the adjusting sleeve 21 to the holding pin 20 against arrow 41 is defined now by the axial length of the vertical section 29 of the L-shaped groove 28. Due to the radial adjusting motion of the holding balls 51, the positive-locking connection between these holding balls 51 and the locking groove 19 of the mounting pin 11 is eliminated, so that the entire holding device 13 is lifted off together with the cover disk 12 that is stationarily in connection with this and the filter sheet 10 located under it can be replaced.

It can be easily imagined that based on the special embodiment, especially of the holding device 13, the pressing disk 12 can be mounted and removed in an extremely simple manner. For mounting, the pressing disk 12 is ultimately placed simply on the mounting pin 11 together with the holding device 13 until the holding surfaces 18 of the profile web 17 come to mesh with the bearing profile 35 of the holding pin 20 in a positive-locking manner. Since a connection of this holding pin 20 with the mounting pin 11 is now achieved, which connection rotates in unison, the pressing disk 12 is likewise arranged on this nonrotatably in relation to the wall section 5. This position can be fixed in a very simple manner by subsequently adjusting the adjusting sleeve 21 in the axial direction indicated by arrow 41 and subsequent rotation in the direction of arrow 59. The pressing disk 12 can, in turn, be lifted off from the filter sheet 10 in a very simple manner by correspondingly reversing these motions, so that the filter sheet can be replaced in a simple manner.

Based on the fixation of the pressing disk 12 via the holding surfaces 18 of the profile web 17 of the mounting pin 11 and the bearing profile 35 of the holding pin 20, the pressing disk 12 is fixed nonrotatably relative to the wall section 5 and hence to the filter sheet 10, so that damage, especially during the mounting of the filter sheet 10, is ruled out with certainty.

While specific embodiments of the invention have been shown and described in detail to illustrate the application of the principles of the invention, it will be understood that the invention may be embodied otherwise without departing from such principles.

What is claimed is:

1. A filter holder for a sterilization container provided in a wall area or in a plurality of wall areas with ventilation openings, through which an exchange of air takes place in the closed state between the interior space of the sterilization container and the surrounding area, wherein the ventilation openings are covered by a filter sheet to form a sterile barrier, which brings about sterilization of air entering the interior space, as a sterilization space, through the ventilation openings, wherein the filter sheet is held on the wall area by an air-permeable pressing disk, the filter holder comprising:

a mounting pin, which protrudes over the wall area and is stationarily connected with the wall area, provided in the wall area of the ventilation openings;

a holding pin with a mounting hole, the holding pin acting on the pressing disk to press the pressing disk against the wall area in the axial direction, the holding pin being attachable to the mounting pin;

a detachable positive-locking connection, connecting the holding pin to the mounting pin; and an adjusting sleeve securing the positive-locking connection, the adjusting sleeve being mounted displaceably on the holding pin.

2. A filter holder in accordance with claim 1, wherein the positive-locking connection between the mounting pin and the holding pin comprises a circular locking groove of the mounting pin and a plurality of holding balls, which are each arranged in a radial through hole of the holding pin, wherein the holding balls are radially adjustable from a neutral radial position, in which they are not in connection with the locking groove of the mounting pin, into a blocked position in which they mesh with the locking groove.

3. A filter holder in accordance with claim 2, wherein:
for being pushed over the holding pin, the adjusting sleeve has, in an end area directed towards the mounting pin, a through hole, which has a circular, radial expansion located in an upper, neutral axial position of the adjusting sleeve on the holding pin in an area of the holding balls, and with a diameter selected to be such that the holding balls can be moved radially into their neutral position; and the through hole has a smaller diameter that can be brought into functional connection with the holding balls during an axial adjustment of the adjusting sleeve on the holding pin into the securing position thereof, such that the holding balls are brought through the through hole into their blocked position in which they protrude into the mounting hole of the holding pin and mesh with the locking groove of the mounting pin.

4. A filter holder in accordance with claim 2, wherein:
in an outer jacket surface, the holding pin has an L-shaped groove forming a vertical section extending in parallel to a central longitudinal axis of the holding pin and a horizontal section extending at right angles thereto;

a through hole, into which a fixing pin can be stationarily inserted, is provided in the side wall of the adjusting sleeve;

the fixing pin passes radially inwardly through the side wall and meshes with the L-shaped groove in the mounted state; and the adjusting sleeve with the fixing pin is brought from a neutral, upper axial position into a lower securing position along the vertical section and is subsequently caused to mesh with the horizontal section by a relative rotation relative to the holding pin with the fixing pin into an axially nondisplaceable locking position.

5. A filter holder in accordance with claim 3, wherein:
in an upper end area, the holding pin has a continuous through hole extending at right angles, in the radially outer end areas of which locking balls are provided, which are pressed radially outwardly by means of an axial compression spring; and the through hole of the adjusting sleeve has a circular fixing groove in an axially upper end area; and the axial arrangement of the through hole in the holding pin and the axial arrangement of the fixing groove in the through hole of the adjusting sleeve are selected to be such that the locking balls lockingly mesh with the fixing groove in the upper, neutral axial position of the adjusting sleeve.

6. A filter holder in accordance with claim 5, wherein:
the through hole of the adjusting sleeve has two mutually diametrically opposed milled recesses axially above its fixing groove; and the circumferential position and axial position of the milled areas of the adjusting sleeve relative to the locking balls of the holding pin are selected to be such that the locking balls lockingly mesh with the milled recesses after the axial adjustment and rotation of the adjusting sleeve into the locking position thereof.

7. A filter holder in accordance with claim 1, wherein the pressing disk is stationarily in connection with the holding pin.

8. A filter holder in accordance with claim 1, wherein:
the mounting pin has, in an end area located towards the wall area, a radially expanded profile web with holding surfaces arranged uniformly distributed on the circumference; and the mounting hole of the holding pin has, in an end area located towards the wall area, a bearing profile, with which the holding pin meshes nonrotatably in its pressed position with the holding surfaces of the profile web.

9. A sterilization container comprising:
a container structure with a wall area with a ventilation opening, through which an exchange of air takes place in a closed state between an interior space of the sterilization container and the surrounding area;

a filter element covering the ventilation opening to form a sterile barrier, which brings about sterilization of air entering the interior space, as a sterilization space, through the ventilation opening;

an air-permeable pressing disk holding the filter element on the wall area;

a filter holder comprising:
a mounting pin, which protrudes over the wall area and is stationarily connected with the wall area, provided in the wall area of the ventilation openings;

a holding pin with a mounting hole, the holding pin acting on the pressing disk to press the pressing disk against the wall area in the axial direction, the holding pin being attachable to the mounting pin;

a detachable positive-locking connection, connecting the holding pin to the mounting pin; and an adjusting sleeve securing the positive-locking connection, the adjusting sleeve being mounted displaceably on the holding pin.

10. A sterilization container in accordance with claim 9, wherein the positive-locking connection between the mounting pin and the holding pin comprises a circular locking groove of the mounting pin and a plurality of holding balls, which are each arranged in a radial through hole of the holding pin, wherein the holding balls are radially adjustable from a neutral radial position, in which they are not in connection with the locking groove of the mounting pin, into a blocked position in which they mesh with the locking groove.

11. A sterilization container in accordance with claim 10, wherein:

for being pushed over the holding pin, the adjusting sleeve has, in an end area directed towards the mounting pin, a through hole, which has a circular, radial expansion located in an upper, neutral axial position of the adjusting sleeve on the holding pin in an area of the holding balls, and with a diameter selected to be such that the holding balls can be moved radially into their neutral position; and the through hole has a smaller diameter that can be brought into functional connection with the holding balls during an axial adjustment of the adjusting sleeve on the holding pin into the securing position thereof, such that the holding balls are brought through the through hole into their blocked position in which they protrude into the mounting hole of the holding pin and mesh with the locking groove of the mounting pin.

12. A sterilization container in accordance with claim 10, wherein:

in an outer jacket surface, the holding pin has an L-shaped groove forming a vertical section extending in parallel to a central longitudinal axis of the holding pin and a horizontal section extending at right angles thereto;

a through hole, into which a fixing pin can be stationarily inserted, is provided in the side wall of the adjusting sleeve;

the fixing pin passes radially inwardly through the side wall and meshes with the L-shaped groove in the mounted state; and the adjusting sleeve with the fixing pin is brought from a neutral, upper axial position into a lower securing position along the vertical section and is subsequently caused to mesh with the horizontal section by a relative rotation relative to the holding pin with the fixing pin into an axially nondisplaceable locking position.

13. A sterilization container in accordance with claim 11, wherein:

in an upper end area, the holding pin has a continuous through hole extending at right angles, in the radially outer end areas of which locking balls are provided, which are pressed radially outwardly by means of an axial compression spring; and the through hole of the adjusting sleeve has a circular fixing groove in an axially upper end area; and the axial arrangement of the through hole in the holding pin and the axial arrangement of the fixing groove in the through hole of the adjusting sleeve are selected to be such that the locking balls lockingly mesh with the fixing groove in the upper, neutral axial position of the adjusting sleeve.

14. A sterilization container in accordance with claim 13, wherein:

the through hole of the adjusting sleeve has two mutually diametrically opposed milled recesses axially above its fixing groove; and the circumferential position and axial position of the milled areas of the adjusting sleeve relative to the locking balls of the holding pin are selected to be such that the locking balls lockingly mesh with the milled recesses after the axial adjustment and rotation of the adjusting sleeve into the locking position thereof.

15. A sterilization container in accordance with claim 9, wherein the pressing disk is stationarily in connection with the holding pin.

16. A sterilization container in accordance with claim 9, wherein:

the mounting pin has, in an end area located towards the wall area, a radially expanded profile web with holding surfaces arranged uniformly distributed on the circumference; and the mounting hole of the holding pin has, in an end area located towards the wall area, a bearing profile, with which the holding pin meshes nonrotatably in its pressed position with the holding surfaces of the profile web.

* * * * *